(12) United States Patent
Radfar et al.

(10) Patent No.: US 11,712,238 B2
(45) Date of Patent: Aug. 1, 2023

(54) DEVICE AND METHOD FOR INTRACORPOREAL AND EXTRACORPOREAL LAPAROSCOPIC SUTURING AND KNOT TYING

(71) Applicants: Forough Gholamreza Hedayat Allah Radfar, Muscat (OM); Mohammad Majid Mohsin Zeinalddin, Muscat (OM); Moein Majid Mohsin Zeinalddin, Muscat (OM)

(72) Inventors: Forough Gholamreza Hedayat Allah Radfar, Muscat (OM); Mohammad Majid Mohsin Zeinalddin, Muscat (OM); Moein Majid Mohsin Zeinalddin, Muscat (OM)

( * ) Notice: Subject to any disclaimer, the term of this patent is extended or adjusted under 35 U.S.C. 154(b) by 158 days.

(21) Appl. No.: 17/159,908

(22) Filed: Jan. 27, 2021

(65) Prior Publication Data
US 2021/0236115 A1    Aug. 5, 2021

Related U.S. Application Data

(60) Provisional application No. 62/969,254, filed on Feb. 3, 2020.

(51) Int. Cl.
*A61B 17/04*    (2006.01)
*A61B 17/062*    (2006.01)

(52) U.S. Cl.
CPC ...... *A61B 17/0469* (2013.01); *A61B 17/0485* (2013.01); *A61B 17/062* (2013.01); *A61B 2017/0474* (2013.01); *A61B 2017/0475* (2013.01)

(58) Field of Classification Search
CPC ............ A61B 17/0469; A61B 17/0485; A61B 17/062; A61B 2017/0474; A61B 2017/0475; A61B 17/0482; A61B 17/0483; A61B 17/12009; D04G 3/00; D04G 3/02; D04G 5/00; B65B 13/26; B65B 13/265; B65H 69/04
See application file for complete search history.

(56) References Cited

U.S. PATENT DOCUMENTS

| | | | | |
|---|---|---|---|---|
| 5,234,443 | A * | 8/1993 | Phan | A61B 17/0469 606/205 |
| 7,666,196 | B1 * | 2/2010 | Miles | A61B 17/0469 606/144 |
| 9,635,847 | B1 * | 5/2017 | Chaney | A01K 91/047 |
| 2011/0172767 | A1 * | 7/2011 | Rathi | A61B 17/0401 156/60 |

* cited by examiner

*Primary Examiner* — Darwin P Erezo
*Assistant Examiner* — Raihan R Khandker (57) ABSTRACT

An apparatus for laparoscopic intracorporeal knot tying includes a needle grasper including a needle holder shaft and a needle holder jaw located at a distal end of the needle holder shaft, and a knot loop grasper including a knot loop holder shaft, which is slidable on the needle holder shaft, and a knot loop holder jaw located at a distal end of the knot loop holder shaft. In an inactive state of the apparatus, the knot loop holder is located proximal to the needle holder jaw. In an active state of the apparatus at a time of a knot tying, the knot loop holder jaw slides on the needle holder shaft toward the distal end of the needle holder shaft and beyond the needle holder jaw to carry components of a knot over a standing end of a suture held by the needle holder jaw.

1 Claim, 8 Drawing Sheets

A- Capsized Granny's Knot

B- Capsized Square knot

C- Capsized Surgeon's knot

D- Nicky's knot a capsized granny-wise surgeon's knot

E- Tennessee slider, a capsized Whatknot

FIG. 4

Duncan Loop knot

Nicky's knot

Tennessee Slider Knot

Roader Knot

SMC knot

Weston Knot

Meltzer Knot

Tay-side Knot

DEVICE AND METHOD FOR INTRACORPOREAL AND EXTRACORPOREAL LAPAROSCOPIC SUTURING AND KNOT TYING

CROSS REFERENCE TO RELATED APPLICATIONS

The present Application is based on and claims priority from U.S. Provisional Patent Application No. 62/969,254 filed on Feb. 3, 2020, the entire content of which is incorporated herein by reference.

FIELD OF THE INVENTION

The present invention relates generally to an innovative laparoscopic knot tying method and an intracorporeal knot tying device designed for facilitating easier intracorporeal knot tying.

Our invented method and device aim to improve the traditional laparoscopic knot tying by simplifying and increasing speed and efficacy of performing the intracorporeal and extracorporeal knot tying. It also reduces the movement of instruments intracorporeally while knot tying in order to reduce chance of trauma to tissues close to site of knot application. In addition, the intracorporeal knot tying device facilitates reduction of the angle between the working instruments while knot tying, so even single port laparoscopic intracorporeal knot tying is possible using this technique and device. Moreover, the method and device are more suitable to ergonomics of laparoscopic operative surgery as compared to traditional method, so this fact reduces fatigability and trauma to surgeon while operating. Furthermore, this method not only simplify accurate knot reproducibility, security and stability, but also it helps reducing the amount of suture material used in knot formation, to decrease foreign body reaction in patient's tissues.

BACKGROUND AND DESCRIPTION OF THE RELATED ART

Any discussion of the prior art throughout the specification should in no way be considered as an admission that such prior art is widely known or forms part of common general knowledge in the field.

Laparoscopic knot tying is the most challenging skill a surgeon must master in transforming from laparotomy to laparoscopic surgery. Many advances and technologies like clips, staples, pre-tied suture loop, tissue adhesives, laser tissue welding, Harmonic, Ligasure, electro-cautery are used in laparoscopic operations to ease the tasks by decreasing the need for knot tying, yet no surgeon can feel confident in attempting laparoscopic surgery before mastering the laparoscopic knot tying and suturing techniques, because as the patient safety is at stake during operation, surgeon cannot exclusively depend on these technologies which have their own limitations in applied surgery and are more expensive and machine dependent.

Surgeons are taught that it is vital to perfect their techniques of knot tying as within the strength of their knots, lay the safety and lives of their patients. The important basic principles of achieving knots with correct configuration, appropriate shaping and maximum security and stability, are related to understanding knot tying techniques.

Figure 1:
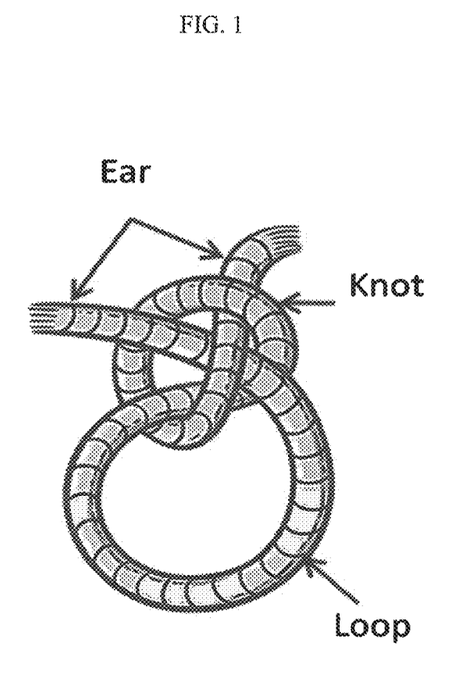
FIG. 1 Shows parts of knot which are named ears, knot, and loop.

Generally, the tied knot has three parts as shown in FIG. 1, The Loop, which embrace the tissue, vessel or the two edges of divided wound which needs to be approximated; The knot, which is composed of a number of throws or winds stacked against each other; The ears which are composed of the Needle-end or post limb of suture and the short limb or working limb. To understand the technique of knot tying and to perform absolutely perfect knot surgeons should master performing three stages of knot tying which are configuration, shaping and knot securing.

a) Configuration:

Configuration means the composition of different components of knot such as throws, winds and half hitches forming the knot. Understanding configurations and various types of knots is essential skill for surgeons to master. Using extra suture and large unnecessary knots will trigger foreign body reaction to suture material inside the tissues. This is why, surgeon should always choose the simplest knot configuration that is suitable to achieve desired strength of tissue approximation without using extra suture.

b) Shaping:

Shaping of the knot depends on many factors. For instance, tension applied on suture while making knot, should be appropriate to make the components of knot tight and secure. If excess tension is applied while staking the knot, it might cause breaking of suture or cut the tissue. If less tension is applied while stacking, an insecure loose knot may form and in a surgical case, it may cause a catastrophe. Another factor affecting shape of knot is "staking" which in surgical term means keeping the components of knot in order one after the other without space or loose suture between them. Another knot shaping variable arise in case different gauge instrument is used for casting the components of knot on standing end.

For example, in art of knitting, different size needles or hooks are used for different size threads. This is because if the size of the thread is not appropriate for diameter of the needle the knot will be too loose or too tight. Hence where hooks or knitting needles are used, the diameter of the instrument should be appropriate for size of suture. The general rule to make reasonably good knot is to have instrument two times the thickness of the suture we use. The bigger the diameter of instrument, the looser the knots especially if more than two throws are used.

Another factor for change in knot shaping and geometry is brought about by direction of traction force applied on each end of suture during knot tying. An important principle in one hand knot tying technique is that after tying the first half hitch, traction on standing end should be maintained to avoid loosening of loop before you make next throws. After we finish each consecutive throw and sliding it down to the knot, we must put traction on both ends equally to changes the slip knot to flat knot configuration and hence we change its character from sliding to non-sliding. If this step to change the sliding configuration to non-sliding flat knot configuration is not done, the knot may slip on standing end and loosen. This is the principal used in past pointing when sliding half hitches are pushed with knot pusher, to flatten the knot and prevent it from slipping.

In laparoscopic knot tying it is important to understand the details of changes in configuration of knot by changing the traction force from one end to another end of the suture. Here we discuss two phenomenon "capsizing" and "flipping".

Figure 2:
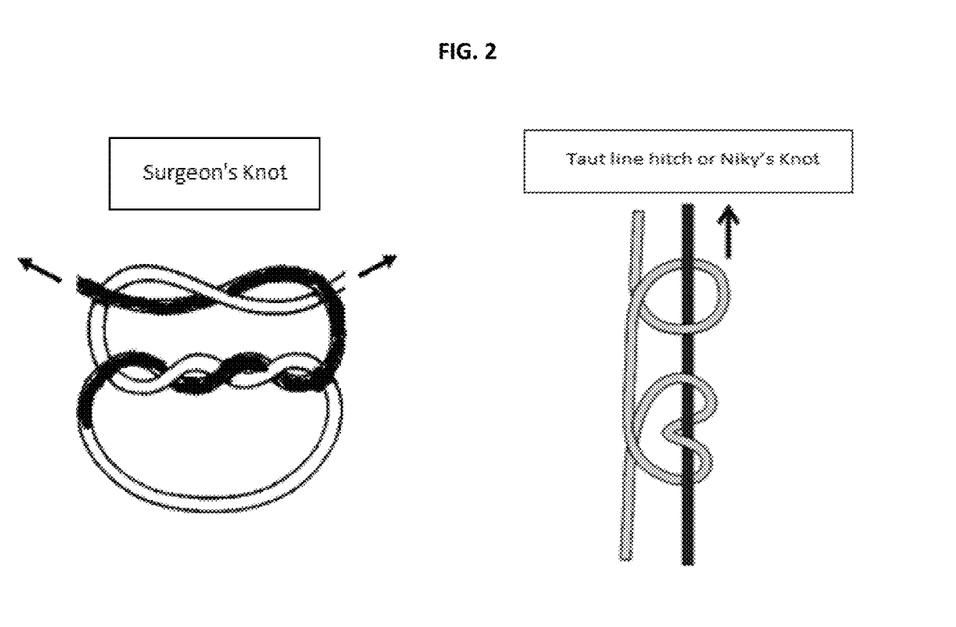
FIG. 2 Shows Taut Line hitch and Nicky's knot are actually the capsized version of surgeons' knot.

Capsizing means flat knot's geometry changes to slip knot geometry as overhand knot changes to half hitch by pulling at one end of suture as standing end. The flat knots used in laparoscopy can become slip knot if their capsized version is used, for example Taut Line hitch and Nicky's knot are actually the capsized version of surgeons' knot as shown in FIG. 2.

Flipping means relocation of knot form working end to standing end and vice versa by interchanging the traction force between these two ends of suture. In case of sliding knot made of half hitches, flipping changes the last half hitch position and make a reverse half hitch on alternating post (RHAP). Flipping is useful in locking and securing the sliding knot by using this method.

c) Knot Securing:

Securing is the final stage of knot tying. The completed knot must be secure, with no chance of slipping. Addition of three to five Reverse Half Hitches on Alternate Posts (RHAP) on the base knot maximize tensile strength and reduce risk of untying. In intracorporeal knot tying after each throw is made, both suture ends should be pulled to opposite direction, parallel to loop of knot, to secure the knot by changing its shape from sliding to flat knot. In case of extracorporeal slip knots, past pointing with knot pusher will shape the half hitches into a flat knot and secure it.

Number of RHAP which is needed for securing the knot is decided by surgeon according to type of suture material and the place the knot is used. For example, the number of reverse half hitches for securing knots made by monofilament suture material need to be more than braided suture materials, to increase length of contact and complexity between suture limbs so as to achieve higher internal interference and more knot security. It is noteworthy to mention that after securing the knot with appropriate RHAPs, additional half hitches will not increase the security of knot, but it increases tissue forging body reaction and knot failure due to material failure (breakage).

There are many laparoscopic ergonomic challenges during suturing and knot tying in addition to visual and tactile obstacles which is mentioned few related ones here. In laparoscopy the ports are fixed, and the freedom of movements is lost. The movement of instruments are around a fulcrum which is the port of entry; it restricts the movement of instruments to only 4 directions which are: rotation, up/down angulation, left/right angulation, in/out movement. The working angle between two instruments should be more than 60 degrees, so the handles of instruments are further apart causing more tension on surgeon arms and shoulders and neck muscles while suturing and knot tying.

During laparoscopy not only the surgeon's movements are restricted, but also all the muscles of arms shoulder, neck and back are activated and under tension, this causes lactic acid production in muscles and tendons and hence disabling muscle pain builds up, because of which the efficiency of surgeon reduces as the time of surgery increases. On the long run many surgeons have acquired permanent serious trauma such as headache, neck pain cervical spondylitis, shoulder pain, finger joint pain in hands, tenosynovitis and hand muscle injury due to performing multiple laparoscopic procedures where suturing and knotting were required.

When the handle of instrument is moved to any direction the tip of instrument moves in opposite direction due to fulcrum effect, it makes hand eye coordination difficulty. Due to decoupling of visual axis and motor axis and two-dimensional perceptions during laparoscopic knot tying a lot of extra movements are made, for example, over shooting of instruments, these imprecisions of movements can cause damage to patient's tissues by the jaws of instruments during the attempts to perform a laparoscopic knot.

Imprecision of movement happens more in hands of less experienced laparoscopic surgeons. The laparoscopic knot tying is classified under extracorporeal and intracorporeal techniques. There are some common laparoscopic knot tying difficulties in traditional methods which is mentioned as their elimination was the aim in inventing a new method for laparoscopic knot tying.

Techniques of intracorporeal knot tying such as expert 'c', Cinch, Smiley, Gladiator and Spaghetti techniques are aimed at forming a square knot, granny's knot or surgical knot as the base knot intracorporeally, followed by few reverse half hitches to secure it. Recently some new techniques also have been introduced for laparo-endoscopic single-site surgery (LESS), such as D-loop. All these laparoscopic techniques aim to use the laparoscopic instruments to imitate surgeon's hands movement in knot tying which is ergonomically difficult for surgeon and can cause trauma to him on repeated prolonged laparoscopic surgeries. The new method using intracorporeal knot tying device can overcome the above ergonomic and technical difficulties. There are two different extracorporeal knot tying techniques which are non-sliding (static) knots and sliding knots. The non-sliding knots are used when surgeon wants to avoid suture sliding through tissue or anchoring device. The major drawback of both, intracorporeal knot tying and non-sliding extracorporeal knot tying, is that the loop may loosen before second throw is placed on first throw to secure it.

In extracorporeal non-sliding knot tying, surgeon must note that if all the half hitches are made keeping the standing end on tension, the knot will have sliding property and is not secure. To achieve knot security the half hitches should be made on alternate posts or fastened by past pointing with knot-pusher to change the configuration of sliding knot to non-sliding knot. The sliding or slip knots, on the other hand, allow the knot to be tied extracorporeally and then it is slid on standing end, with a knot-pusher to the site where knot is to be applied. There are many types of slip knots Roeder knot, Duncan Knot, Nicky's knot, Weston knot, Meltzer knot, SMS knot, Tayside knot.

The main drawback of the sliding knot or slip knot tying technique is that its components should be stacked properly on the standing end otherwise its shape and configuration will change, as a result of this, either it will not slide on standing end or its loops are loose so they will form a faulty knot which does not have the property of intended slip knot. In addition, these loose knots allow more suture material to be left at surgical site causing more forging body reaction and increase chance of inflammation and infection. To make the proper configuration of slip knot using working end on the standing end using gloved hands during surgery needs a lot of practice and skill as both suture ends are thin, soft and highly mobile. In addition, gloved hands have less tactile sensation so these factors increase the chances of faulty sliding knot formation during laparoscopic extracorporeal knot tying.

In view of ergonomic difficulties, disadvantages, and drawbacks of the aforementioned methods of laparoscopic knot tying, it is an exemplary purpose of the present invention to introduce a new method of laparoscopic knot tying. Technique of intracorporeal knot tying using intracorporeal knot tying device and Technique of extracorporeal sliding knot tying using extracorporeal knot tying loop guide or needle guide helps in overcoming the mentioned obstacles and simplifying accurate properly slacked, secure and stable laparoscopic knots.

SUMMARY OF THE INVENTION

Figure 5:
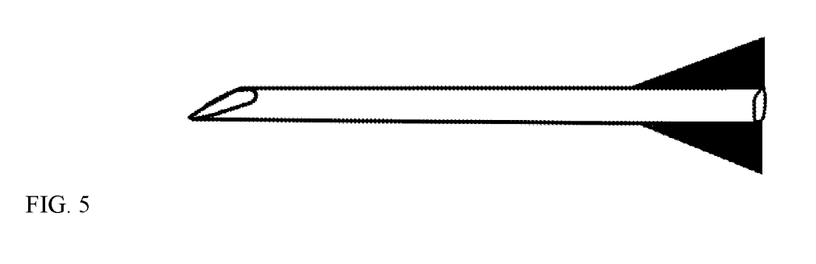
FIG. 5 Shows extracorporeal knot tying needle guide. A blunt hollow needle like rode guide with proximal end to the distal end and a longitudinal access channel extending from the proximal end to the distal, and a hollow plastic/metallic handle wrapped around the proximal end to allow for holding the apparatus and inserting the surgical suture material inside the needle through its distal oval cut section. The diameter of the hallow needle should be about one and half times the size of thickness of suture material used.

This invention is related to an innovative laparoscopic knot tying method. The invention also relates to a device for intracorporeal knot tying shown in FIG. 7, FIG. 8, FIG. 9, FIG. 10 and FIG. 11. For facilitating extracorporeal knot tying, two devices were designed namely, extracorporeal knot tying loop knot guide shown in FIG. 6 and extracorporeal knot tying needle guide as seen in FIG. 5.

The invented method and devices aim to improve the traditional laparoscopic knot tying by simplifying and increasing speed and efficacy of performing the intracorporeal and extracorporeal knot tying. It also reduces the movement of instruments intracorporeally while knot tying in order to reduce chance of trauma to tissues close to site of knot application. In addition, the intracorporeal knot tying device facilitates reduction of the angle between the working instruments while knot tying, so even single port laparoscopic intracorporeal knot tying is possible using this technique and device. Moreover, the method and device are more suitable to ergonomics of laparoscopic operative surgery as compared to traditional method, so this fact reduces fatigability and trauma to surgeon while operating. Furthermore, this method is not only simplifying accurate knot reproducibility, security and stability, but also it helps reducing the amount of suture material used in knot formation, to decrease foreign body reaction in patient's tissues.

Figure 11:
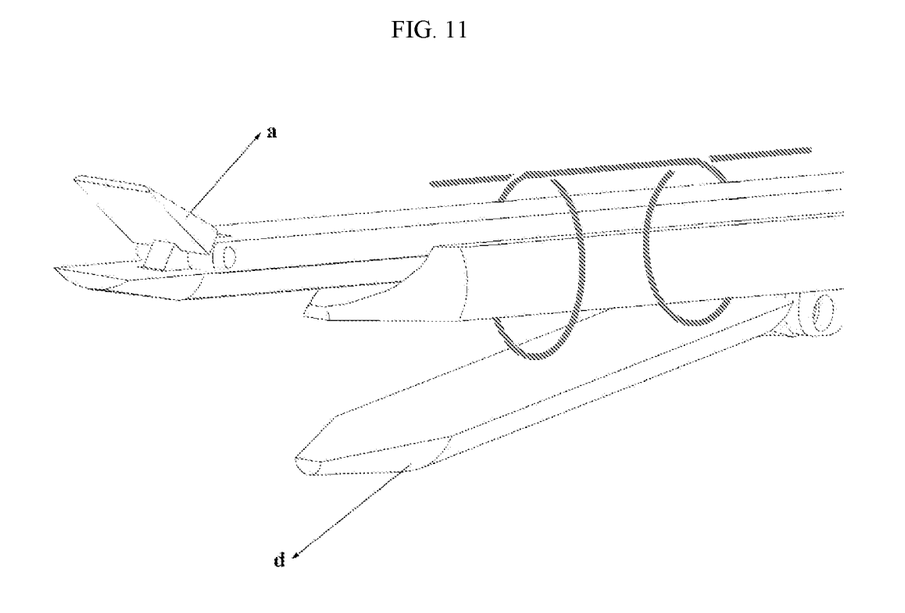
FIG. 11 Diagrammatic illustration of an enlarged view of front portion of the instrument, showing the needle holder jaws 'a', knot loop holder jaws 'b' and how the capsized loops of a knot is casted on the shaft of the device and between jaws of loop holder 'b' by the working end of suture.
Figure 12:
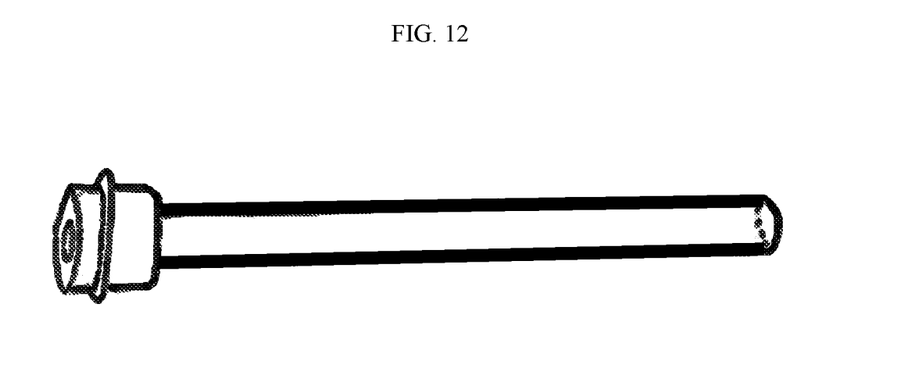
FIG. 12 shows the metal reducer through which needle holder or the intracorporeal knot tying device should pass before casting the knot loops on its shaft and holding them by knot loop holder jaw, by working end of suture. The needle holder holds the standing end of suture 1 cmm away from needle. Both jaws of the intracorporeal knot tying device and the suture needle complex are fully withdrawn into the cavity of the metal reducer so that metal reducer will prevent damage to the suture material and distortion of knot loops on device while introducing the intracorporal knot tying device and suture, into the body through a suitable canula place in entry port.

1. Intracorporeal Knot Tying Method:

The intracorporeal knot tying device is passed through a metal tube reducer, which is having a rubber stopping to prevent the scape of gas from body cavity once it is introduced into the laparoscopic port of entry, as shown in FIG. 12. Working end of suture is casted in form of capsized configuration of the square knot or surgical knot shown in FIG. 11, on the shaft of the invented intracorporeal knot tying device in such way that the capsized loops are grasped within the knot loop holder jaws of the device.

The needle end of suture is held by the needle holder jaw of the device one cm away from the needle (In case it is desired to make a free tie around a structure, hold the standing end, one and half cm away from its end, with needle holder jaws). Both jaws of the intracorporeal knot tying device and the suture needle complex are fully withdrawn into the cavity of the metal reducer so that metal reducer will prevent damage to the suture material while introducing the intracorporal knot tying device and suture, into the body, through the suitable canula placed in entry port.

After introducing the intracorporeal knot tying device and suture complex into the body the needle holder jaw holds the needle in appropriate position, the needle is passed through the tissue (or in case of making a knot around continuous structure, when needle holder jaws holding standing end of suture, passes under the structure which should be tied) a grasper introduced through another port, is used to hold the needle or standing end and pulls the suture, then the needle end or standing end is held with needle holding jaws of the intracorporeal knot tying device again, one cm away from needle.

The casted knot loops on shaft of intracorporeal knot tying device held in knot loop holder jaws is moved forward over the shaft of device by moving loop holder handle forward, 2-3 cm beyond the needle holding jaw of the device. A grasper introduced through another port, now holds the working short end of suture, to avoid loops from unwinding. The knot loop holder jaws release the loops of knot on the standing end of suture which is now held with the needle holder jaws, and the loop holder jaws are moved back to their position on the shaft of intracorporeal knot tying device, by moving the loop holder handle of device backward to its original position.

The needle holder pulls the standing end of suture; this will allow the slip knot formed by short working end to slide on standing end and tighten the knot loop. Then steps for shaping and securing the knot are performed. This base knot is secured from loosening or dismantling by flipping which means interchanging the tension from needle end of suture (standing end) to the short distal end of suture or loop end or working end; this will ideally change the shape of the knot, from sliding to a flat knot. By changing shape of the knot, the property of knot changes from a sliding knot to a strong non-sliding knot which is more secure.

Then both sides of suture are pulled with equal force horizontally in opposite direction of, to further tighten the base knot and further strengthen the knot and prevent it from slipping or loosening. As the first and second throw of the surgeon's knot or square knot are simultaneously applied as a sliding knot which with flipping it is changed to non-sliding knot, this method is superior to the traditional method of intracorporeal knot tying as there is no chance of loosening the loop of knot between the application of first throw and second throw, more over this method simplify and increasing speed and efficacy of performing the intracorporeal knot tying. It also reduces the movement of instruments intracorporeally while knot tying hence it reduces chance of trauma to tissues close to site of knot application by unnecessary movement of instruments while trying to make first and second throw.

In addition, the intracorporeal knot tying device facilitates reduction of the angle between the working instruments while knot tying, so even single port laparoscopic intracorporeal knot tying is possible using this technique and device. Moreover, the method and device are more suitable to ergonomics of laparoscopic operative surgery as compared to traditional method, so this fact reduces fatigability and trauma to surgeon while operating.

Furthermore, this method not only simplifying accurate knot reproducibility, security and stability, but also it helps reducing the amount of suture material used in knot formation, to decrease foreign body reaction in patient's tissues. This invented method is an exemplary method of intracorporeal knot tying. Throwing few reverse half hitches, on this base knot will guaranty the security of knot from slipping or unwinding. The number of the reverse half hitches is decided according to the type of suture material and type of knot applied in the particular situation, by the surgeon.

Figure 3:
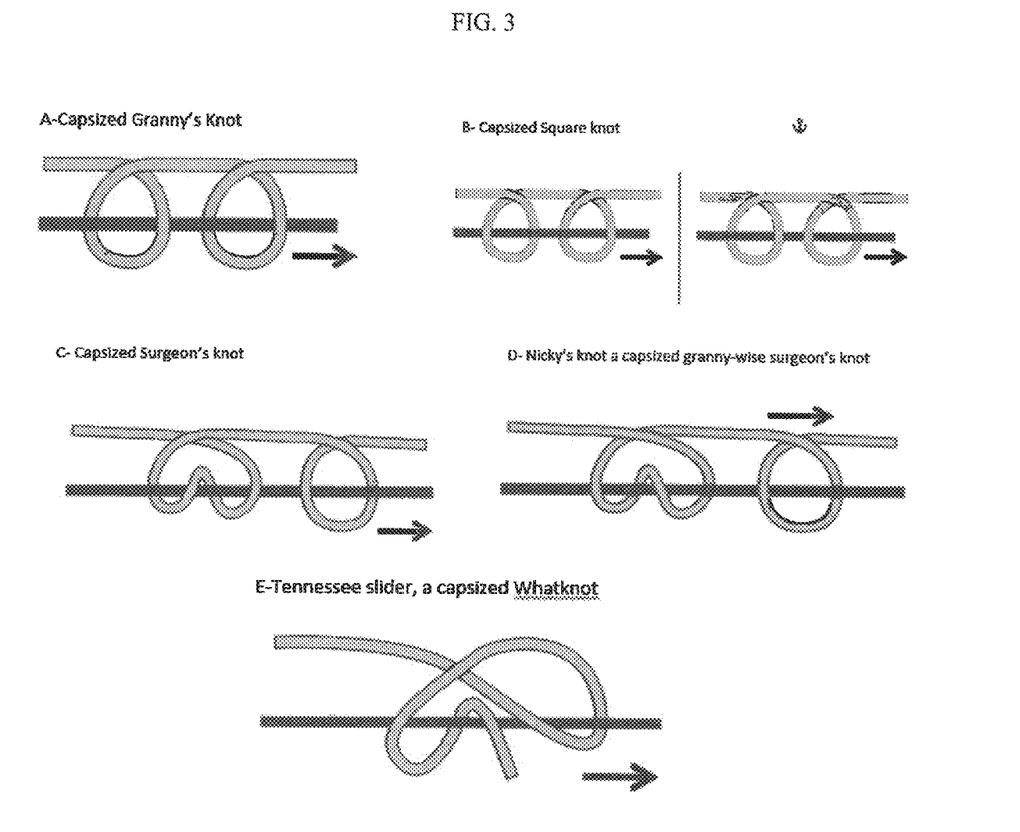
FIG. 3 Shows the capsized geometry of flat knots (A) capsized granny knot, (B) capsized square knot, (C) capsized surgeon's knot, (D) Nicky's knot a capsized granny-wise surgeon's knot, and (E) the Tennessee slider, a capsized what knot.
Figure 4:
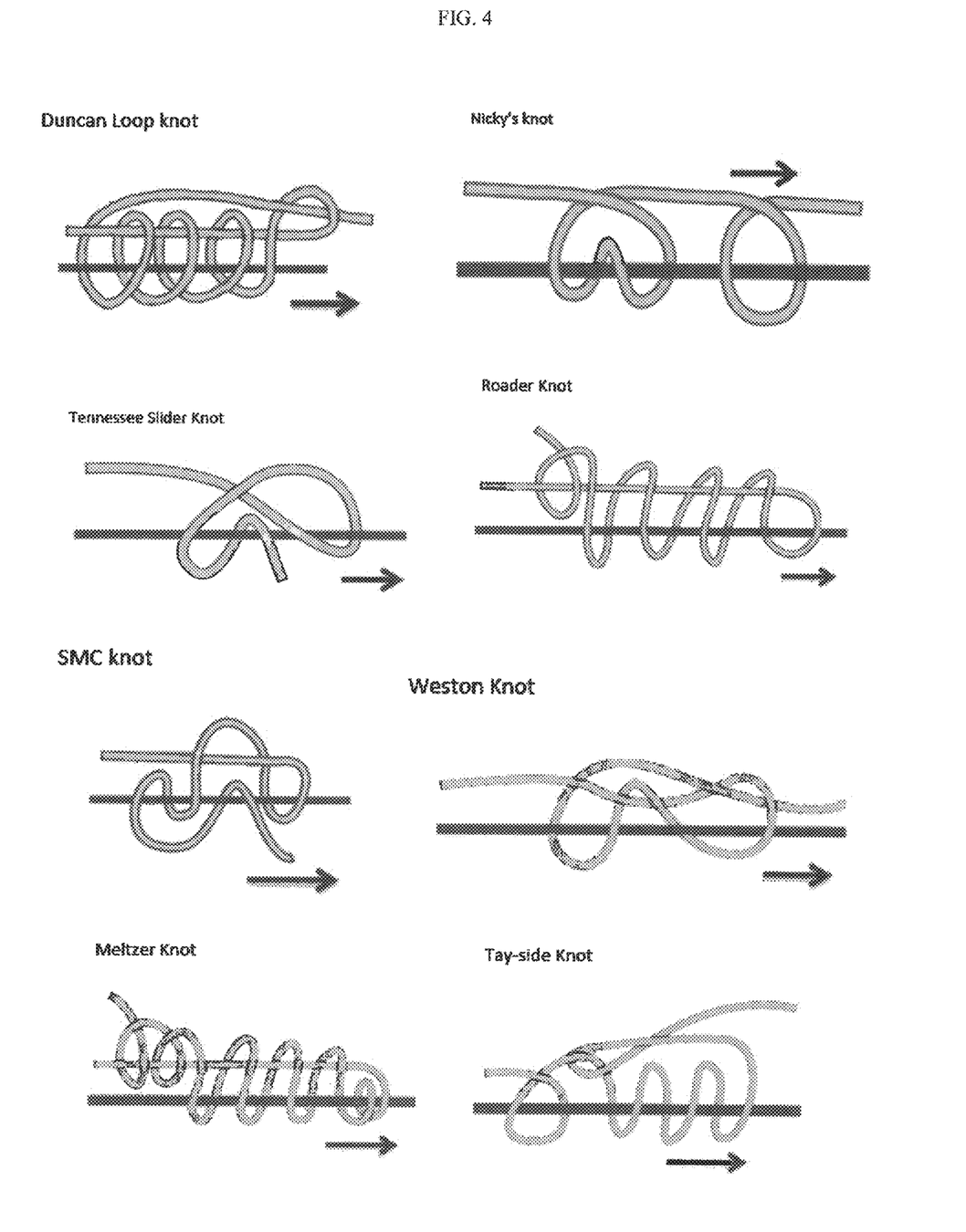
FIG. 4 Shows commonly used compound sliding knots, Duncan loop knot, Nicky's knot, Tennessee Slider knot, Roader knot, SMC knot, Weston knot, Meltzer knot, Tayside knot.

2. Extracorporeal Knot Tying Method:

Extracorporeal knots are tied outside the body by standing end and working end of suture. The knot is slipped on to the required site were the knot should be placed intracorporeally using a knot pusher. In this technique of extracorporeal knot tying, the standing end of suture is passed through the cavity of appropriate size needle guide or it is passed between the two prongs of the appropriate size loop guide, the working end or loop end of suture is casted on shaft of loop guide or a Needle guide in form of capsized configuration of selected sliding/slip knot, the standing end is passed through the casted working end using loop or needle guide, to form a sliding knot. The capsized configuration of flat knots such as Square knot, Granny's knot, surgeon's knot, Granny wise Surgeon's knot/Nicky's knot, Tennessee slider or What knot, which can be used as sliding knot are shown in FIG. 3 and FIG. 4, diagrammatically.

In case of using needle guide; the standing end is passed through the cavity of needle guide and after the working end is casted over the guide in form of capsized configuration of selected sliding/slip knot, if needle guide is pulled out of the embracing working end loops the standing end is left lying neatly within loops of working end, forming the slip knot with it.

In case of using loop guide; the standing end is passed through the two arms of loop guide and pushed to the end at the point of U-turn of the arms of loop guide, the working end is casted over the loop guide arms in form of capsized configuration of selected sliding/slip knot, the loop guide is pulled out through the casted working end carrying with it the standing end of the suture. Thus, the standing end lay neatly within cased loops of the working end and they forming the sliding knot together.

Forming the components of knot directly over standing end with working end of the thin suture material while wearing gloves during surgery is very difficult and there are high chances of imprecise knot formation. This method of using a metal needle or loop guide to form the capsized components of various knots on it, instead of directly forming the components of knot on the standing end as the traditional method, is very helpful during surgery to achieve appropriate stacking of components of knots over stiff guide so the sliding knots are made with precise and correct configuration extracporeally. And as within the safety of our knots lies the safety of our patients, this is an exemplary method of extracorporeal knot tying.

BRIEF DESCRIPTION OF THE DRAWINGS

It is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. The drawings herein are meant to be illustrative, and the design of the inventive assembly is not limited to that disclosed herein but may be modified within the spirit and scope of the present invention. Also, none of the drawings is necessarily to scale.

DETAILED DESCRIPTION OF THE EXEMPLARY ASPECTS OF THE INVENTION

The present disclosure provides a device and method for knot tying which helps simplifying and increasing speed and efficacy of performing the intracorporeal and extracorporeal knot tying by reducing the movement of instruments intracorporeally while knot tying in order to reduce chance of trauma to tissues close to site of knot application.

Furthermore, the technique disclosed in this invention facilitates reduction of the angle between the working instruments while knot tying such that single port laparoscopic intracorporeal knot tying is possible. The disclosed invention also provides with suitability to ergonomics of laparoscopic operative surgery to reduce fatigability and trauma to surgeon by simplifying accurate knot reproducibility, security and stability. One advantage of the disclosed invention is that it helps reducing the amount of suture material used in knot formation and therefore decreases foreign body reaction in patient's tissues.

FIG. 1 shows parts of knot which are named ears, knot, and loop. FIG. 2 shows Taut Line hitch and Nicky's knot are actually the capsized version of surgeons' knot. FIG. 3 shows the capsized geometry of flat knots (A) capsized granny knot, (B) capsized square knot, (C) capsized surgeon's knot, (D) Nicky's knot a capsized granny-wise surgeon's knot, and (E) the Tennessee slider, a capsized what knot.

FIG. 4 shows commonly used compound sliding knots, Duncan loop knot, Nicky's knot, Tennessee Slider knot, Roader knot, SMC knot, Weston knot, Meltzer knot, Tayside knot. FIG. 5 shows extracorporeal knot tying needle guide. A blunt hollow needle like rode guide with proximal end to the distal end and a longitudinal access channel extending from the proximal end to the distal, and a hollow plastic/metallic handle wrapped around the proximal end to allow for holding the apparatus and inserting the surgical suture material inside the needle through its distal oval cut section. The diameter of the hallow needle should be about one and half times the size of thickness of suture material used.

Figure 6:
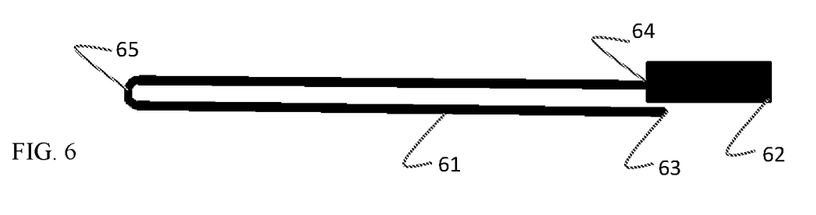
FIG. 6 Shows Extracorporeal knot tying loop guide. A u-shaped solid metallic rod guide. The diameter of the cross-section of rod should be about the size of the stature material used. A plastic or metallic handle attached at one arm end proximally.

FIG. 6 shows Extracorporeal knot tying loop guide. A u-shaped solid metallic rod guide 61 includes a u-shaped edge 65 in a distal end, a first arm with a first arm end 64 in a proximal end of the rod guide 61, and a second arm with a second arm end 63 that is blunt and free in the proximal end of the rod guide 61. The diameter of the cross-section of rod 61 should be about the size of the stature material used. A plastic or metallic handle 62 is attached at the first arm end 64 proximally.

Figure 7:
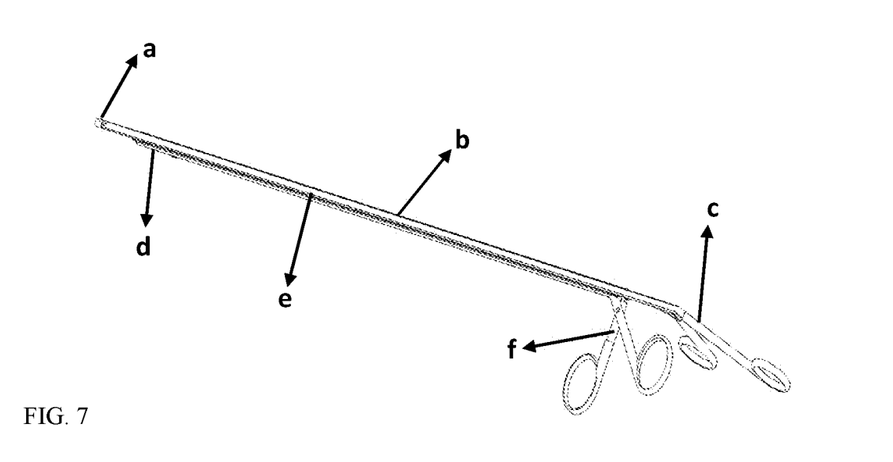
FIG. 7 Illustrates an exemplary device for intracorporeal knot tying in accordance with an exemplary aspect of the present invention; Side view; lateral view of the intracorporeal knot tying device in accordance with the present disclosure; a-Needle holder jaw, b-Needle holder shaft, c-The needle holder handle with incorporated locking mechanism controlling needle holder jaw, d-knot loop holder jaw, e-Knot loop holder shaft, which is mobile on the shaft of needle holder, f-The knot loop holder handle with incorporated locking mechanism controlling the loop holder jaw. Shaft of the loop holder can move axially forward and backward along the shaft of the needle holder.

FIG. 7 illustrates an exemplary device for intracorporeal knot tying in accordance with an exemplary aspect of the present invention, side view, the lateral view of the intracorporeal knot tying device in accordance with the present disclosure, a—Needle holder jaw, b—Needle holder shaft, c—The needle holder handle with incorporated locking mechanism controlling needle holder jaw, d—knot loop holder jaw, e—Knot loop holder shaft, which is mobile on the shaft of needle holder, f—The knot loop holder handle with incorporated locking mechanism controlling the loop holder jaw. Shaft of the loop holder can move axially forward and backward along the shaft of the needle holder.

Figure 8:
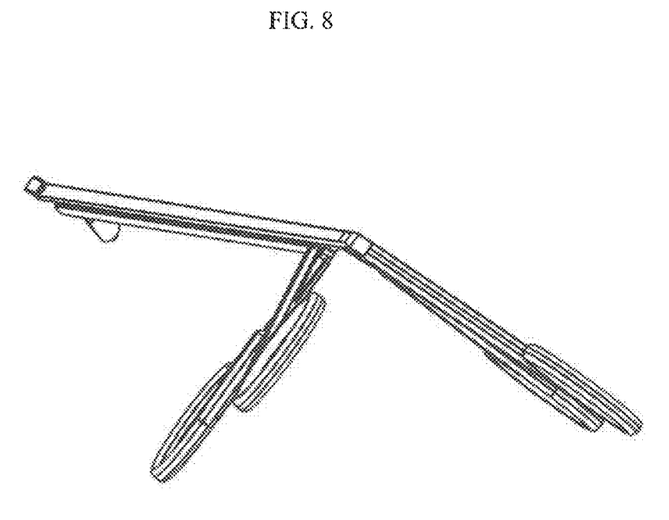
FIG. 8 Illustrates the exemplary device for intracorporeal knot tying in accordance with an exemplary aspect of the present invention; back view. Shows the relationship of the needle holder handle and loop holder handle at right angle to one another to suit the ergonomic of device as disclosed.
Figure 9:
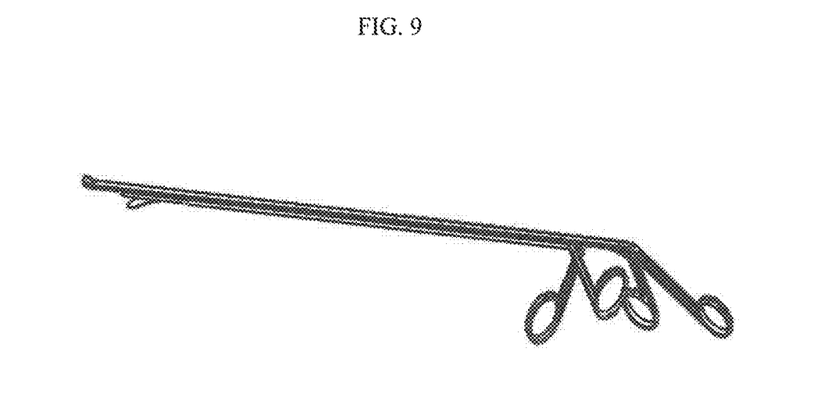
FIG. 9 Illustrates an exemplary device for intracorporeal knot tying in accordance with an exemplary aspect of the present invention; Side view.

FIG. 8 illustrates the exemplary device for intracorporeal knot tying in accordance with an exemplary aspect of the present invention, back view. FIG. 8 further shows the relationship of the needle holder handle and loop holder handle at right angle to one another to suit the ergonomic of device as disclosed. FIG. 9 illustrates an exemplary device for intracorporeal knot tying in accordance with an exemplary aspect of the present invention, side view.

Figure 10:
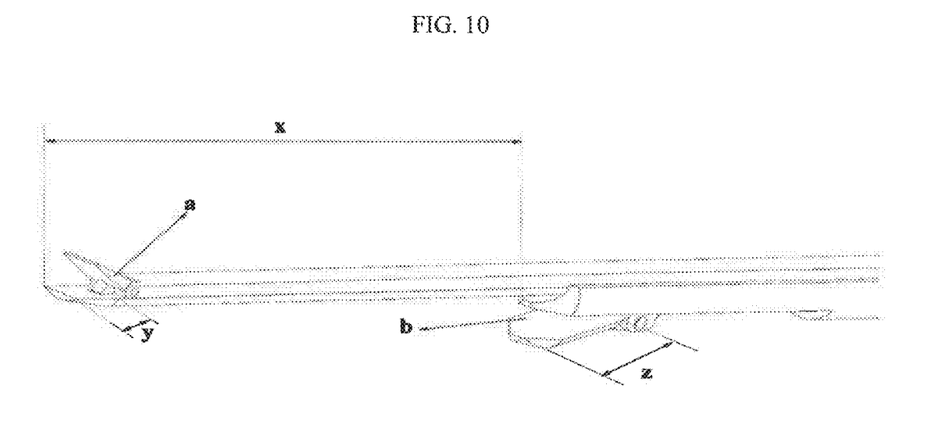
FIG. 10 Diagrammatic illustration of an enlarged view of front portion of the instrument, showing the needle holder jaws 'a', knot loop holder jaws 'b' with jaws open.

FIG. 10 diagrammatic illustration of an enlarged view of front portion of the instrument, showing the needle holder jaws 'a', knot loop holder jaws 'b' with jaws open. FIG. 11 diagrammatic illustration of an enlarged view of front portion of the instrument, showing the needle holder jaws 'a', knot loop holder jaws 'b' and how the capsized loops of a knot is casted on the shaft of the device and between jaws of loop holder 'b' by the working end of suture.

FIG. 12 shows the metal reducer through which needle holder or the intracorporeal knot tying device should pass before casting the knot loops on its shaft and holding them by knot loop holder jaw, by working end of suture. The needle holder holds the standing end of suture 1 cmm away from needle. Both jaws of the intracorporeal knot tying device and the suture needle complex are fully withdrawn into the cavity of the metal reducer so that metal reducer will prevent damage to the suture material and distortion of knot loops on device while introducing the intracorporal knot tying device and suture, into the body through a suitable canula place in entry port.

One embodiment of this invention is a device invented for intracorporeal knot tying as shown in FIG. 7. It is a device which is made up of combination two graspers, needle holder grasper and knot loop holder grasper, which are conjoined together in a single common shaft. The common shaft of the device is made up of a static needle holder shaft "b" on which the shaft of knot loop holder "e" can slide back and forth. The shaft of knot loop holder "e" is mobile and can slide back and forth over the shaft of needle holder "b".

The device has two jaws, needle holder jaw "a" and knot loop holder jaw "d", situated on the shaft of the device as shown in FIG. 7 and FIG. 10. The jaw of the knot loop holder "d" is situated proximal to the jaw of needle holder "a" on shaft of the device, in inactive state. The jaw of the knot loop holder "d" can slide on the shaft beyond the jaws of needle holder jaw "a" at time of knot tying process, to carry the components of knot over the standing end of the suture held by the needle holder jaw.

After releasing the components of knot over the standing end by opening its jaws, it will slide back to its prior inactive position on the shaft of the device. Both the jaws "a" and "d" have a non-mobile jaw which is fixed along the shaft and the mobile jaw which can open and close using the handle "c" and "f" respectively.

The handles controlling needle holder "c" and knot loop holder "f" are situated at an angle to one another for ergonomic comfort during surgery as shown in FIG. 8. Each handle has an individual lock designed on them. This angulation between the handles enables a right-handed surgeon to hold needle holder handle with right hand and maneuver the loop holder handle with left hand. In case of left-handed person, the instrument can be made with handle of the loop holder "f" on the right side of the needle holder handle "c". The handle of loop holder "f" can slide the loop holder shaft forward and backward on the shaft of needle holder.

The drawings herein are meant to be illustrative, and the design of the inventive assembly is not limited to that disclosed herein but may be modified within the spirit and scope of the present invention.

Another exemplary embodiment of this invention is devices designed to be used for extracorporeal knot tying.

1) Extracorporeal knot tying loop guide shown in FIG. 6, a U-shaped solid metallic rod guide. The diameter of the cross-section of rod should be about the size of the stature material used. FIG. 6. Diameter of the loop knot guide should be proportionate to the suture used. It should be ideally as close as possible to thickness of the suture used. If it is too thick the components of knot will be arranged very loosely on the standing end (faulty knot), if it is too thin, it cannot create enough space for the standing end to pass though the components of knot formed on it by the running end.

2) Extracorporeal knot tying Needle guide shown in FIG. 5, extracorporeal knot tying needle guide; A blunt hollow needle like rode guide with proximal end to the distal end and a longitudinal access channel extending from the proximal end to the distal; and a hollow handle wrapped around the proximal end to allow for holding the apparatus and inserting the surgical suture material inside the needle through its distal oval cut section. The diameter of the hallow needle should be proportionate to the suture used.

It should be about one and half times the size of thickness of suture material used. The diameter of bore should be just enough to allow the desired suture pass through it. The blunt tip through which the standing end of suture is passed should be cut at an angle to the long axis of the needle guide to allow easy passage of suture through the oval opening in FIG. 5.

Another exemplary embodiment of this invention is innovative method of extracorporeal and intracorporeal knot tying as described below.

3. Intracorporeal Knot Tying Method:

Another exemplary embodiment of this invention describes an intracorporeal knot tying technique using intracorporeal knot tying device. The method of intracorporeal knot tying includes the following:

(A) The intracorporeal knot tying device is passed through a metal tube reducer, which is having a rubber stopping to prevent the scape of gas from body cavity once it is introduced into the laparoscopic port of entry, as shown in FIG. 12.

(B) Working end of suture is casted in form of capsized configuration of the square knot or surgical knot shown in FIG. 11, on the shaft of the invented intracorporeal knot tying device in such way that the capsized loops are grasped within the knot loop holder jaws of the device.

(C) Needle end of suture is held by the needle holder jaw of the device one cm away from the needle (In case it is desired to make a free tie around a structure, hold the standing end, one and half cm away from its end, with needle holder jaws).

(D) Both jaws of the intracorporeal knot tying device and the suture needle complex are fully withdrawn into the cavity of the metal reducer so that metal reducer will prevent damage to the suture material while introducing the intracorporal knot tying device and suture, into the body, through a canula placed in entry port.

(E) After introducing the intracorporeal knot tying device and suture complex into the body the needle holder jaw holds the needle in appropriate position, the needle is passed through the tissue (or in case of making a knot around continuous structure, when needle holder jaws holding standing end of suture, passes under the structure which should be tied).

(F) a grasper introduced through another port, is used to hold the needle or standing end at its exit and pulls the suture, then the needle end or standing end is held with needle holding jaws of the intracorporeal knot tying device again, one cm away from needle.

(G) The casted knot loops on shaft of intracorporeal knot tying device held in knot loop holder jaws is moved forward over the shaft of device by moving loop holder handle forward, beyond the needle holding jaw of the device.

(H) The grasper introduced through another port, now holds the short working end to avoid loops from unwinding, once they are released from knot loop holder.

(I) The knot loop holder jaws release the loops of knot on the standing end of suture which is held with the needle holder jaws, and the loop holder jaws are moved back to their position on the shaft of intracorporeal knot tying device, by moving the loop holder handle of device backward to its original position.

(J) The needle holder jaws pull the standing end of suture; this will allow the slip knot formed by short working end to slide on standing end and tighten the knot loops.

(K) Then steps for shaping and securing the knot are performed. This base knot is secured from loosening or dismantling by flipping which means interchanging the tension from needle end of suture (standing end) to the short distal end of suture or loop end or working end; this will ideally change the shape of the knot, from sliding to a flat knot. By changing shape of the knot, the property of knot changes from a sliding knot to a strong non-sliding knot which is more secure. Then both sides of suture are pulled with equal force horizontally in opposite direction of, to further tighten the base knot and further strengthen the knot and prevent it from slipping or loosening.

As the first and second throw of the surgeon's knot or square knot are simultaneously applied as a sliding knot which with flipping it is changed to non-sliding knot, this method is superior to the traditional method of intracorporeal knot tying as there is no chance of loosening the loop of knot between the application of first throw and second throw, more over this method simplify and increasing speed and efficacy of performing the intracorporeal knot tying. It also reduces the movement of instruments intracorporeally while knot tying hence it reduces chance of trauma to tissues close to site of knot application by unnecessary movement of instruments while trying to make first and second throw.

In addition, the intracorporeal knot tying device facilitates reduction of the angle between the working instruments while knot tying, so even single port laparoscopic intracorporeal knot tying is possible using this technique and device. Moreover, the method and device are more suitable to ergonomics of laparoscopic operative surgery as compared to traditional method, so this fact reduces fatigability and trauma to surgeon while operating. Furthermore, this method not only simplifying accurate knot reproducibility, security and stability, but also it helps reducing the amount of suture material used in knot formation, to decrease foreign body reaction in patient's tissues.

This invented method is an exemplary method of intracorporeal knot tying.

(L) Throwing few reverse half hitches, on this base knot will guarantee the security of knot from slipping or unwinding. The number of the reverse half hitches is decided according to the type of suture material and type of knot applied in the particular situation, by the surgeon.

4. Extracorporeal Knot Tying Method:

Another exemplary embodiment of this invention describes an extracorporeal knot tying technique using extracorporeal knot tying needle guide or loop guide device. Extracorporeal knots are tied outside the body by standing end and working end of suture. The knot is slipped on to the required site were the knot should be placed intracorporeally using a knot pusher. In this technique of extracorporeal knot tying, the standing end of suture is passed through the cavity of appropriate size needle guide or it is passed between the two prongs of the appropriate size loop guide, the working end or loop end of suture is casted on shaft of loop guide or a Needle guide in form of capsized configuration of selected sliding/slip knot, the standing end is passed through the casted working end using loop or needle guide, to form a sliding knot.

The capsized configuration of flat knots such as Square knot, Granny's knot, surgeon's knot, Granny wise Surgeon's knot/Nicky's knot, Tennessee slider or what knot, which can be used as sliding knot are shown in FIG. 3. various types pf compound sliding knots are utilized in extracorporeal knot tying including:

(1) Non-locking such as Duncan loop knot, which resists slipping by tightness of its wrappings of loop end around the post line;
(2) Proximal locking such as Nicky's knot;
(3) Middle locking knot such as SMC Knot, Tennessee slider knot; and (4) Distal locking such as Weston knot, Roeder knot s, Meltzer knot (specially was designed by Meltzer for PDS suture) shown in, Tayside knot (resistant to reverse slippage equivalent to surgeon's knot) are shown in FIG. 4.

In case of using needle guide; the standing end is passed through the cavity of needle guide and after the working end is casted over the guide in form of capsized configuration of selected sliding/slip knot, if needle guide is pulled out of the embracing working end loops the standing end is left lying neatly within loops of working end, forming the slip knot with it.

In case of using loop guide; the standing end is passed through the two arms of loop guide and pushed to the end at the point of U-turn of the arms of loop guide, the working end is casted over the loop guide arms in form of capsized configuration of selected sliding/slip knot, the loop guide is pulled out through the casted working end carrying with it the standing end of the suture. Thus, the standing end lay neatly within casted loops of the working end and they forming the sliding knot together.

Forming the components of knot directly over standing end with working end of the thin suture material, while wearing gloves during surgery is very difficult and there is high chance of imprecise knot formation. This method of using a metal needle or loop guide to form the capsized components of various knots on it, instead of directly forming the components of knot on the standing end as the traditional method, is very helpful during surgery to achieve appropriate stacking of components of knot over stiff guide so the sliding knots are made with precise and correct configuration extracorporeally.

And as within the safety of our knots lies the safety of our patients, this is an exemplary method of extracorporeal knot tying. The slip note is shaped and then slid on the standing end by knot pusher to the site where the knot is to be applied as base knot. Sliding knots without securing with reverse half hitches on alternate post (RHAPs) have low force to failure, so steps for securing the knot are performed. To secure sliding knots, few RHAPs are applied. Each half hitch should be secured by changing its shape from sliding to flat knot using knot pusher by past-pointing technique.

In case of especially arthroscopic knots, to prevent sliding, usually 3 RHAP are thrown after the sliding knot, half hitches should be flipped to tighten, by past-pointing to prevent loosening of the knot. The number of the reverse half hitches is decided according to the type of suture material, the type of base knot and the enforcement required in the particular situation by surgeon.

Advantage of this technique to traditional extracorporeal knot tying is that the components of knot are precisely casted and stacked on the shaft of needle guide or loop guide by working end before the standing end is guided through them. There is less chance of faulty knot formation, and as a result a well-formed absolutely right knot can be formed. There is minimal foreign body tissue reaction as minimal amount of suture material remains in tissue in form of knot.

The descriptions of the various exemplary embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Further, Applicant's intent is to encompass the equivalents of all claim elements, and no amendment to any claim of the present application should be construed as a disclaimer of any interest in or right to an equivalent of any element or feature of the amended claim.

What is claimed is:

1. A method of making an extracorporeal sliding knot, the method comprising:
   providing a loop knot guide comprising a u-shaped wire that comprises a u-shaped edge in a distal end, a first arm, and a second arm ending at a proximal end,
      wherein a first arm end includes a handle, and a second arm end is blunt and free;
   providing a suture with a standing end and a working end extracorporeally;
   inserting the standing end in a space within the u-shaped wire and pushing the standing end towards an end of an inner side of the u-shaped edge;
   wrapping the working end around the first arm and the second arm to form a sliding knot configuration; and
   pulling the standing end of the suture entrapped within the u-shaped edge proximally through component loops formed by the working end over the first arm and the second arm to form the sliding knot configuration extracorporeally.

* * * * *